US00PP21057P2

(12) United States Plant Patent
Krassenberg

(10) Patent No.: US PP21,057 P2
(45) Date of Patent: Jun. 8, 2010

(54) ***IMPATIENS* PLANT NAMED 'SILT SALM09'**

(50) Latin Name: *Impatiens walleriana*
Varietal Denomination: Silt Salm09

(75) Inventor: Jolanda Krassenberg, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 65 days.

(21) Appl. No.: 12/313,346

(22) Filed: Nov. 19, 2008

(51) Int. Cl.
*A01H 5/00* (2006.01)

(52) U.S. Cl. ..... Plt./317

(58) Field of Classification Search ..... Plt./317
See application file for complete search history.

(56) References Cited

U.S. PATENT DOCUMENTS

PP15,908 P2 * 8/2005 Jonkers ..... Plt./317
PP18,029 P2 * 9/2007 Jonkers et al. ..... Plt./317

OTHER PUBLICATIONS

UPOV ROM GTITM Computer Database, GTI Jouve Retreival Software 2009/05 Citation for 'Silt SalmO9'.*

* cited by examiner

*Primary Examiner*—Wendy C. Haas
(74) *Attorney, Agent, or Firm*—S. Matthew Edwards

(57) ABSTRACT

A new *Impatiens* plant named 'Silt Salm09,' particularly distinguished by the salmon-orange flower color, rose-like flower shape, medium green foliage, about medium growth vigor, and low mounded plant habit with good branching.

1 Drawing Sheet

Latin name of the genus and species of the plant claimed: *Impatiens walleriana.*

Varietal denomination: 'Silt Salm09'.

BACKGROUND OF THE NEW PLANT

The present invention comprises a new *Impatiens*, botanically known as *Impatiens walleriana,* and hereinafter referred to by the variety name 'Silt Salm09'.

'Silt Salm09' is a product of a planned breeding program. The new cultivar 'Silt Salm09' has salmon-orange, double-type flowers, medium green foliage, and a well branching plant habit.

'Silt Salm09' originated from a pollination made in July 2005 in a controlled breeding program in Andijk, Netherlands. The parent was an unpatented hybrid seedling identified as 'ID03-455-7' with rose, single-type flowers. It was used as seed and pollen parent. In contrast to its parent, 'Silt Salm09' has a more orange hue of flower color, double-type flowers with more petals and somewhat deeper green foliage.

The seeds were sown in October 2005. 'Silt Salm09' was selected as one flowering plant within the progeny of the stated cross in November 2005 in a controlled environment in Andijk, Netherlands.

The first act of asexual reproduction of 'Silt Salm09' was accomplished when vegetative cuttings were taken from the initial selection in the spring of 2006 in a controlled environment in Andijk, Netherlands.

Horticultural examination of plants grown from cuttings of the plant initiated in the spring of 2006 in Andijk, Netherlands, and continuing thereafter, has demonstrated that the combination of characteristics as herein disclosed for 'Silt Salm09' are firmly fixed and are retained through successive generations of asexual reproduction.

'Silt Salm09' has not been observed under all possible environmental conditions. The phenotype may vary significantly with variations in environment such as temperature, light intensity and day length.

Plant Breeder's Rights for this cultivar were applied for in Canada on Dec. 24, 2007 and in the European Union on Jul. 21, 2008. 'Silt Salm09' has not been made publicly available more than one year prior to the filing of this application.

DESCRIPTION OF THE DRAWINGS

The accompanying photographic drawing shows typical flower and foliage characteristics of 'Silt Salm09' with colors being as true as possible with an illustration of this type. The photographic drawing, taken in late May 2008, shows a 15 week old greenhouse grown plant of the new variety.

DETAILED BOTANICAL DESCRIPTION

The measurements were taken in Hillscheid, Germany, mainly in late May 2008 on 14-15 week old plants that were growing on benches in a greenhouse. Culture of these plants had started around February 10 when rooted cuttings were potted in 12 cm pots and grown at moderately warm temperatures, between 15 and 20° C. in daytime.

Color Chart used: Royal Horticultural Society Colour Chart (R.H.S.) 2001.

BRIEF SUMMARY OF INVENTION

The following observations, measurements, and comparisons describe plants grown in a greenhouse in Hillscheid, Germany and in Andijk, Netherlands. The following traits have been repeatedly observed and are determined to be basic characteristics of the new variety. The combination of these characteristics distinguishes this *Impatiens* as a new and distinct variety.

1. Salmon-orange, double-type flowers.
2. Floriferous habit.
3. Medium green foliage, ovate to elliptical leaves.
4. About medium plant size.

5. Suitable as a bedding plant, for containers and as a flowering pot plant indoors.

COMPARISON WITH COMMERCIAL CULTIVARS

'Silt Salm09' differs from 'Silte Sal07,' (unpatented) by a higher number of branches, more floriferous habit, and smaller leaves.

'Silt Salm09' differs from 'Didi Salmon Two,' U.S. Plant Pat. No. 15,908, by its slightly less pink hue of flower color, less dark green foliage, and by its generally more compact habit with shorter internodes.

Plant:

*Form, growth and habit.*—Mounding, nearly semi-spherically shaped, about medium sized.

*Plant height.*—9-11 cm.

*Plant height (inflorescence included).*—10-12 cm.

*Plant width.*—26-28 cm.

*Plant size in late summer (30 weeks old).*—21-24 cm in height, 35-40 cm in diameter Stem:

*Number of branches.*—13-15.

*Color of stem.*—Light green, RHS 146D or 147C, near the nodes infused with a little anthocyanin: RHS 185C.

*Length of stem.*—About 9-13 cm.

*Diameter.*—5-7 mm at mid portion.

*Length of internodes.*—1.5-4 cm.

*Texture.*—Smooth, glabrous.

Foliage:

*Arrangement.*—Mainly alternate.

*Immature, leaf color, upper surface.*—RHS 137B.

*Lower surface.*—RHS 138A-B with splotches of RHS 186B.

*Mature, leaf color, upper surface.*—RHS 137B to 137C, medium green, dull.

*Lower surface.*—RHS 138B with weak splotches of RHS 186C.

*Length.*—6.0-7.6 cm.

*Width.*—3.8-4.5 cm.

*Shape.*—Elliptical to ovate, pinnate venation.

*Base shape.*—Acute.

*Apex shape.*—Acuminate.

*Margin.*—Slightly crenate, ciliate.

*Texture.*—Glabrous, smooth, apart from the veins protruding on the lower side.

*Color of veins, upper surface.*—RHS 146A, hardly visible.

*Color of veins, lower surface.*—RHS 146C.

Petiole:

*Color upper surface.*—Mainly RHS 186C to 186D.

*Color lower surface.*—RHS 145B to 145C, possibly traces of RHS 186D.

*Length.*—1.5-3.5 cm.

*Diameter.*—0.3 cm.

*Texture.*—Most parts smooth, glabrous.

Inflorescence:

*Duration of flowering.*—Continuous flowering from spring through fall.

*Start of flowering.*—About 6 weeks after planting of rooted cuttings.

*Inflorescence type.*—Emerging from the upper nodes of the stem, peduncle usually bearing 2 flowers.

*Number of flowers and buds per stem.*—About 10 in various stages of development.

Peduncle:

*Color.*—Light green, RHS 145A.

*Length.*—Approximately 2-3 cm.

*Diameter.*—2-2.5 mm.

*Texture.*—Flexible, glabrous.

Pedicel:

*Color of pedicel.*—RHS 145A to 146D.

*Length of pedicel.*—Approximately 2.0-2.5 cm.

*Diameter of pedicel.*—2 mm.

*Texture.*—Smooth, glabrous.

Flower:

*Form.*—Double-type.

*Shape of corolla.*—Round outline, rose-like shape.

*Number of petals.*—More than 20.

*Overall color.*—Salmon orange, appears uniform.

*Upper surface color.*—RHS 43C, may turn RHS 52B with maturing.

*Markings.*—Tiny violet-purple macule at the bases of lower petals, RHS 77B, weak.

*Lower surface color.*—RHS 52B-52C.

*Diameter of flower.*—4.2-4.8 cm.

*Depth (vertical diameter) of flower.*—2-2.5 cm.

*Fragrance.*—None.

*Rain tolerance.*—Fair, but placing it under light rain protection enhances flower quality.

Petals:

*Shape.*—Banner petal cordate, lateral and lower petals obovate.

*Apex shape.*—Emarginate for the banner petal, rounded for most of the others.

*Base.*—Acute.

*Margin.*—Entire.

*Size of outer petals.*—Size of top ('banner') petal: Length: 1.7 cm. Width: 2.7 cm. Size of lateral petals: Length: 1.8-2.0 cm. Width: 1.7-1.8 cm. Size of lower petals: Length: 2.3-2.4 cm. Width: 2.1-2.2 cm. Inner petals are diminishing in size. Petal texture: Glabrous, smooth.

Bud (just before opening):

*Shape.*—Ovoid.

*Length.*—1.6 cm.

*Diameter.*—1.5 cm.

Calyx:

*Number of sepals.*—5, one of which is transformed into a spur.

*Sepal shape.*—Largest one fused with underside of banner petal, lateral sepals narrow, lanceolate, lower sepals fused, ovate and bearing the spur.

*Apex shape.*—Acute to acuminate.

*Base shape.*—Rounded.

*Margins.*—Entire.

*Color of lateral sepals.*—Green, RHS 143B.

*Color of lower sepals.*—Semi-transparent, near RHS 145B.

*Length of lateral sepals.*—5-6 mm.

*Width of lateral sepals.*—1.2 mm.

*Length of lower sepals.*—1.2 cm.

*Width of lower sepals.*—0.4-0.5 cm.

*Texture.*—Very thin, film-like, glabrous.

Spur:

*Aspect of spur.*—Slanting downwards.

*Length of spur.*—3.2-3.6 cm.

*Diameter of spur.*—2 mm near base, thinner towards tip.

*Color of spur.*—Near base RHS 8D to N170D at the tip.

Reproductive organ: Usually none, only occasionally in rudimental form, as all stamen are transformed into petals.

*Fertility/seed set.*—Infertile, no seed set observed.

Disease/pest resistance: Disease resistance or susceptibility has not been observed on this hybrid.

What is claimed is:

1. A new and distinct variety of *Impatiens* plant named 'Silt Salm09' substantially as illustrated and described herein.

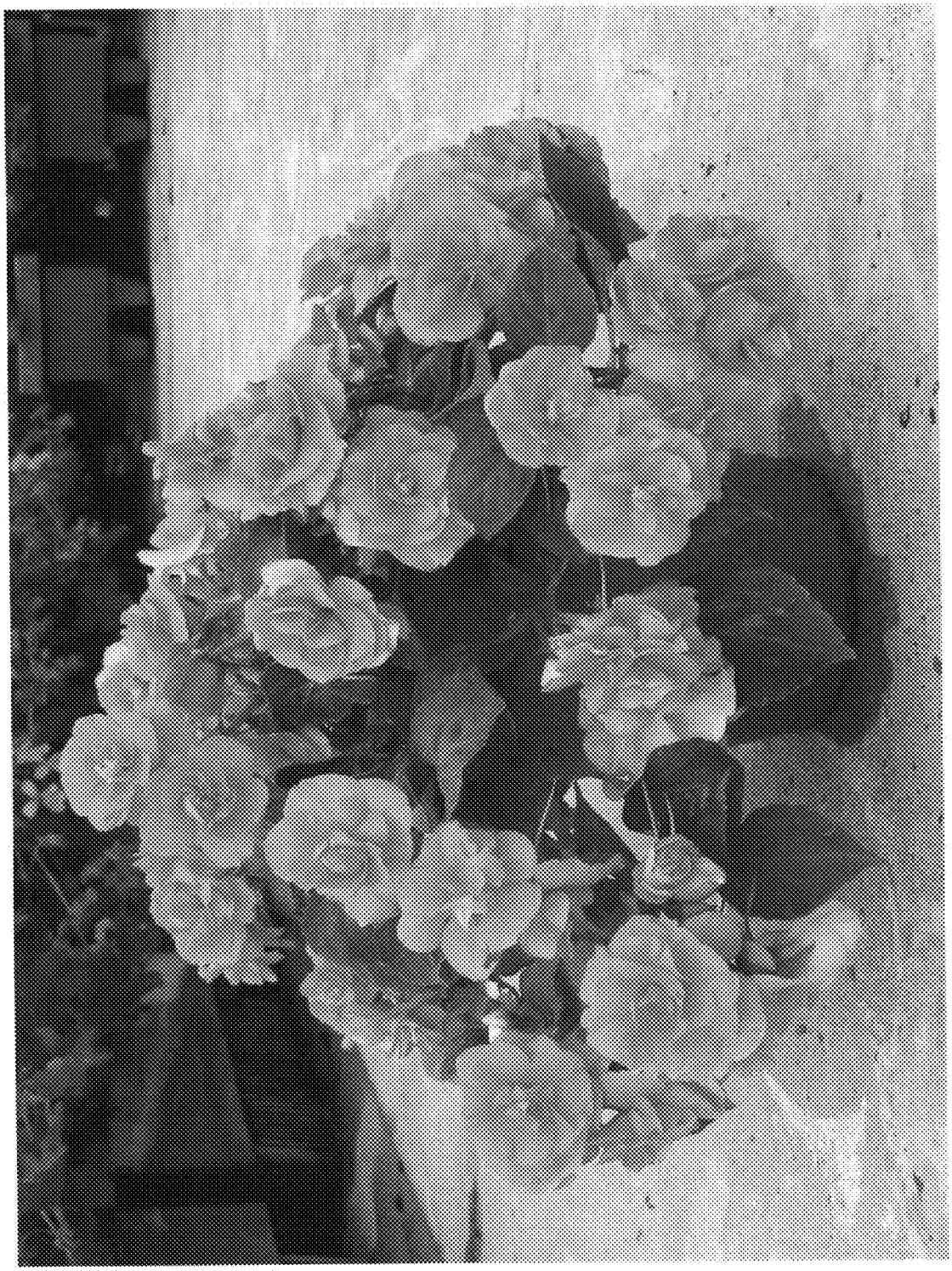

* * * * *